United States Patent
Pentyala

(10) Patent No.: US 9,518,105 B2
(45) Date of Patent: Dec. 13, 2016

(54) POLYPEPTIDES DERIVED FROM CALCITONIN RECEPTORS AND METHODS OF USE

(75) Inventor: Srinivas Pentyala, South Setauket, NY (US)

(73) Assignee: The Research Foundation For The State University of New York, Albany, NY (US)

( * ) Notice: Subject to any disclaimer, the term of this patent is extended or adjusted under 35 U.S.C. 154(b) by 147 days.

(21) Appl. No.: 13/992,005

(22) PCT Filed: Dec. 7, 2011

(86) PCT No.: PCT/US2011/063707
§ 371 (c)(1),
(2), (4) Date: Sep. 3, 2013

(87) PCT Pub. No.: WO2012/078734
PCT Pub. Date: Jun. 14, 2012

(65) Prior Publication Data
US 2013/0345138 A1    Dec. 26, 2013

Related U.S. Application Data

(60) Provisional application No. 61/420,969, filed on Dec. 8, 2010.

(51) Int. Cl.
| | | |
|---|---|---|
| *A61K 38/10* | (2006.01) |
| *C07K 7/08* | (2006.01) |
| *C07K 14/72* | (2006.01) |
| *A61P 19/08* | (2006.01) |
| *A61P 19/10* | (2006.01) |
| *C07K 14/705* | (2006.01) |
| *A61K 38/00* | (2006.01) |

(52) U.S. Cl.
CPC ............ *C07K 14/723* (2013.01); *A61K 38/10* (2013.01); *C07K 7/08* (2013.01); *C07K 14/705* (2013.01); *A61K 38/00* (2013.01)

(58) Field of Classification Search
None
See application file for complete search history.

(56) References Cited

U.S. PATENT DOCUMENTS

| 5,516,651 A | 5/1996 | Goldring et al. |
| 2002/0034785 A1 | 3/2002 | Soppet et al. |
| 2003/0176656 A1 | 9/2003 | Mandell et al. |

FOREIGN PATENT DOCUMENTS

| JP | 2002-095488 | 4/2002 |
| KR | 10-2009-0126061 | 12/2009 |

OTHER PUBLICATIONS

Albrandt et al., Endocrinology, 1995, vol. 136(12):5377-5384 (abstract).*
Ritter et al., Nat. Rev. Mol. Cell Biol., 2009, vol. 10(12):819-830.*

* cited by examiner

*Primary Examiner* — Xiaozhen Xie
(74) *Attorney, Agent, or Firm* — Occhiuti & Rohlicek LLP

(57) ABSTRACT

The present invention is based, in part, on our discovery of compositions and methods that can be used to treat a patient who has a compromised bone (due, for example, to a disease such as osteoporosis or an injury such as a bone fracture). The compositions can also be administered prophylactically. For example, they can be administered to help maintain bone health as a patient ages. More specifically, the compositions include polypeptides that constitute (or that include) a fragment of a calcitonin receptor (CR) and polypeptides that constitute (or include) biologically active variants of those fragments. Sequence-specific formulas are provided herein, and polypeptides conforming to those formulas, as well as nucleic acids encoding them, expression vectors, host cells, pharmaceutical formulations, and methods of their preparation and use are within the scope of the present invention.

17 Claims, 3 Drawing Sheets

```
1   mrftftsrcl alflllnhpt pilpafsnqt yptiepkpfl yvvgrkkmmd aqykcydrmq
61  qlpayqgegp ycnrtwdgwl cwddtpagvl syqfcpdyfp dfdpsekvtk ycdekgvwfk
121 hpennrtwsn ytmcnaftpe klknayvlyy laivghslsi ftlvislgif vffrslgcqr
181 vtlhknmflt yilnsmiiii hlvevvpnge lvrrdpvsck ilhffhqymm acnyfwmlce
241 giylhtlivv avftekqrlr wyyllgwgfp lvpttihait ravyfndncw lsvethllyi
301 ihgpvmaalv vnffflvniv rvlvtkmret heaeshmylk avkatmilvp llgiqfvvfp
361 wrpsnkmlgk iydyvmhsli hfqgffvati ycfcnnevqt tvkrqwaqfk iqwnqrwgrr
421 psnrsaraaa aaaeagdipi yichqelrne pannqgeesa eiiplniieq essa
    (SEQ ID NO:~~34~~) 44
```

FIG. 1

```
Rabbit        KRQWVQFKIQWNQRW-GRR  (SEQ ID NO:~~25~~)45
Mouse         KRQWTQFKIQWSQRW-GRR  (SEQ ID NO:~~26~~)46
Rat           KRQWAQFKIQWSHRW-GRR  (SEQ ID NO:~~27~~)47
Pig           KRQWNQYQAQ---RWAGRR  (SEQ ID NO:~~29~~)48
Human         KRQWAQFKIQWNQRW-GRR  (SEQ ID NO:~~24~~)49

Scrambled 1          WQRQKIWAFQNW   (SEQ ID NO:~~35~~)50
Scrambled 2          WQFNAWQWRIQK   (SEQ ID NO:36)
Scrambled 3          WQFQIRQANKWW   (SEQ ID NO:37)
Scrambled 4          NFWQWWIQARKQ   (SEQ ID NO:38)
```

FIG. 2

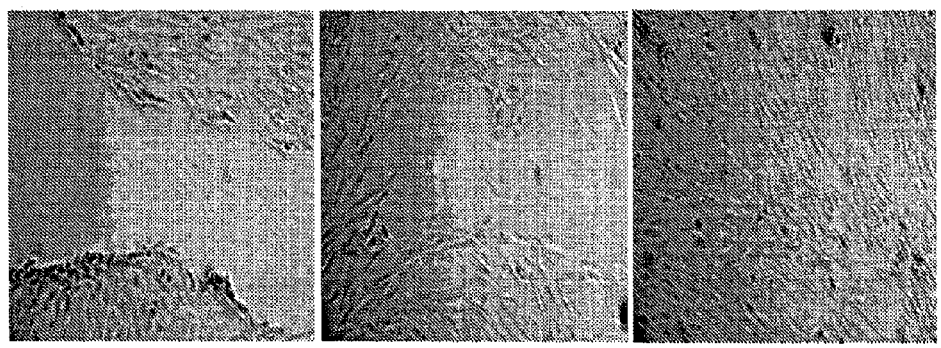

FIG. 3

POLYPEPTIDES DERIVED FROM CALCITONIN RECEPTORS AND METHODS OF USE

CROSS-REFERENCE TO RELATED APPLICATIONS

This application is a U.S. national phase application of the international application PCT/US2011/063707, filed Dec. 7, 2011, which claims the benefit of U.S. Provisional Application No. 61/420,969, which was filed Dec. 8, 2010. With regard to any U.S. applications or patents that claim the benefit of that priority date, the entire content of U.S. Provisional Application No. 61/420,969 is hereby incorporated by reference in its entirety.

The present application contains a Sequence Listing that has been submitted in ASCII format via EFS-Web and is hereby incorporated by reference into the present specification in its entirety. The .txt file was created on Dec. 2, 2015; is named 50089-009US1_SSL; and is 20,999 bytes in size.

FIELD OF THE INVENTION

This invention relates to methods of treating patients who have a disorder or injury that affects a bone, and more particularly to methods of making and using polypeptides derived from a calcitonin receptor to treat compromised bone.

BACKGROUND

Osteoporosis is one of the unfortunate sequelae of increased life expectancy and is a chronic disorder that predisposes individuals to fractures. Approximately 10 million Americans alone have osteoporosis and about 34 million more have an increased risk of developing osteoporotic fractures because of low bone mass. Thus, just over half of the people in the U.S. that are over 50 years old are at risk. Recent advances have led to the introduction of many drugs to treat osteoporosis. However, many patients still have an inadequate clinical outcome and remain at risk.

Studies of osteoporosis are likely to consider the dynamics of bone remodeling; osteoclasts mediate bone resorption and osteoblasts mediate bone formation. Bone remodeling regulates calcium homeostasis in that, bone resorption by the osteoclasts releases stored calcium into the systemic circulation, and bone formation by osteoblasts fixes circulating calcium in its mineral form. Disrupting this balance between bone resorption and formation can result in various bone pathologies in which bone mineral density (BMD) is reduced, bone micro architecture is disrupted, and the amount and variety of non-collagenous proteins in bone is altered.

SUMMARY

The present invention is based, in part, on our discovery of compositions and methods that can be used to treat a patient who has a compromised bone (due, for example, to a disease such as osteoporosis or an injury such as a bone fracture). The compositions can also be administered prophylactically. For example, they can be administered to help maintain bone health as a patient ages. More specifically, the compositions include polypeptides that constitute (or that include) a fragment of a calcitonin receptor (CR) and polypeptides that constitute (or include) biologically active variants of those fragments. The CR can be any CR that is naturally expressed. For example, a polypeptide of the invention can include a sequence that is identical to the sequence of a portion of a CR expressed in a mammalian cell (e.g., a human cell, a non-human primate cell, a rodent cell (e.g., a mouse, rat, hamster, or gerbil cell), a canine cell, a feline cell, a porcine cell, a bovine cell, or a CR of another mammalian cell). Further, the CR may be of any isoform (e.g., isoform 1, isoform 2, or isoform 3). As noted, instead of including a naturally occurring fragment, the polypeptide can include a sequence that is a biologically active variant of a naturally occurring CR sequence. For ease of reading, we will not repeat phrases such as "or a biologically active variant thereof" at every opportunity. It is to be understood that where a polypeptide that constitutes or includes a naturally occurring fragment of a CR is useful, a variant that retains sufficient biological activity to function in the methods of the invention can also be used.

In one aspect, the polypeptide of the invention consists of or includes a fragment of a calcitonin receptor or a biologically active variant thereof, the amino acid sequence of the polypeptide conforming to Formula (I):

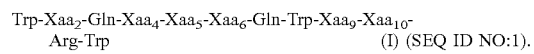

Trp-Xaa$_2$-Gln-Xaa$_4$-Xaa$_5$-Xaa$_6$-Gln-Trp-Xaa$_9$-Xaa$_{10}$-Arg-Trp  (I) (SEQ ID NO:1).

In Formula (I), Xaa$_2$ is Ala, Val, Thr, or Asn; Xaa$_4$ is Phe or Tyr; Xaa$_5$ is Lys or Gln; Xaa$_6$ is Ile or Ala; Xaa$_9$ is Asn or Ser; and Xaa$_{10}$ is Gln or His. In particular embodiments, Xaa$_2$ can be Ala; Xaa$_4$ can be Phe; Xaa$_5$ can be Lys; Xaa$_6$ can be Ile; Xaa$_9$ can be Asn or Ser; and Xaa$_{10}$ can be Gln. It will be evident from the formula that certain Trp, Gln, and Arg residues are invariant. While the invention is not limited to polypeptides that function according to any one given molecular mechanism, it is our current understanding that the invariant residues (as shown in Formula I and the other formulas provided herein) are linked to functionality. To produce a biologically active variant of Formula I, the carboxy-terminal Trp residue can be omitted. The residues within the polypeptides can be selected independently of one another or in view of one another. In these embodiments and any others described herein, the polypeptide can be substantially pure.

A polypeptide of the invention can conform to Formula (I) and can further include at least one additional glutamate (Glu) or pyroglutamate (pGlu) residue at the amino terminus of the polypeptide. A polypeptide of the invention can include the amino acid triplet Lys-Arg-Gln at the amino terminus of the polypeptide. In that event, the amino acid sequence of the polypeptide would conform to: Lys-Arg-Gln-Trp-Xaa$_2$-Gln-Xaa$_4$-Xaa$_5$-Xaa$_6$-Gln-Trp-Xaa$_9$-Xaa$_{10}$-Arg-Trp (SEQ ID NO:2), with the unspecified residues selected from those listed above. The carboxy terminal may also be extended. For example, the carboxy terminal of the polypeptide can further include the amino acid triplet Gly-Arg-Arg. In that event the amino acid sequence of the polypeptide would conform to: Trp-Xaa$_2$-Gln-Xaa$_4$-Xaa$_5$-Xaa$_6$-Gln-Trp-Xaa$_9$-Xaa$_{10}$-Arg-Trp-Gly-Arg-Arg (SEQ ID NO:3). In these embodiments and any others described herein, the carboxy terminus of the polypeptide can be amidated. The invention encompasses variants of these polypeptides and any others described herein (e.g., the polypeptides shown in Table 1) in which the carboxy-terminal residues (e.g., Trp or Arg) have been omitted.

More specifically, a polypeptide of the invention can have an amino acid sequence that is identical to or that includes an amino acid sequence shown in Table 1. Alternatively, the polypeptide can be, or can include, a biologically active variant of one of these amino acid sequences.

TABLE 1

| Sequence | |
|---|---|
| Trp-Ala-Gln-Phe-Lys-Ile-Gln-Trp-Asn-Gln-Arg-Trp | (SEQ ID NO: 4) |
| Trp-Val-Gln-Phe-Lys-Ile-Gln-Trp-Asn-Gln-Arg-Trp | (SEQ ID NO: 5) |
| Trp-Thr-Gln-Phe-Lys-Ile-Gln-Trp-Ser-Gln-Arg-Trp | (SEQ ID NO: 6) |
| Trp-Ala-Gln-Phe-Lys-Ile-Gln-Trp-Ser-His-Arg-Trp | (SEQ ID NO: 7) |
| Glu/pGlu-Trp-Ala-Gln-Phe-Lys-Ile-Gln-Trp-Asn-Gln-Arg-Trp | (SEQ ID NO: 8) |
| Glu/pGlu-Trp-Val-Gln-Phe-Lys-Ile-Gln-Trp-Asn-Gln-Arg-Trp | (SEQ ID NO: 9) |
| Glu/pGlu-Trp-Thr-Gln-Phe-Lys-Ile-Gln-Trp-Ser-Gln-Arg-Trp | (SEQ ID NO: 10) |
| Glu/pGlu-Trp-Ala-Gln-Phe-Lys-Ile-Gln-Trp-Ser-His-Arg-Trp | (SEQ ID NO: 11) |
| Lys-Arg-Gln-Trp-Ala-Gln-Phe-Lys-Ile-Gln-Trp-Asn-Gln-Arg-Trp | (SEQ ID NO: 12) |
| Lys-Arg-Gln-Trp-Val-Gln-Phe-Lys-Ile-Gln-Trp-Asn-Gln-Arg-Trp | (SEQ ID NO: 13) |
| Lys-Arg-Gln-Trp-Thr-Gln-Phe-Lys-Ile-Gln-Trp-Ser-Gln-Arg-Trp | (SEQ ID NO: 14) |
| Lys-Arg-Gln-Trp-Ala-Gln-Phe-Lys-Ile-Gln-Trp-Ser-His-Arg-Trp | (SEQ ID NO: 15) |
| Trp-Ala-Gln-Phe-Lys-Ile-Gln-Trp-Asn-Gln-Arg-Trp-Gly-Arg-Arg | (SEQ ID NO: 16) |
| Trp-Val-Gln-Phe-Lys-Ile-Gln-Trp-Asn-Gln-Arg-Trp-Gly-Arg-Arg | (SEQ ID NO: 17) |
| Trp-Thr-Gln-Phe-Lys-Ile-Gln-Trp-Ser-Gln-Arg-Trp-Gly-Arg-Arg | (SEQ ID NO: 18) |
| Trp-Ala-Gln-Phe-Lys-Ile-Gln-Trp-Ser-His-Arg-Trp-Gly-Arg-Arg | (SEQ ID NO: 19) |
| Glu/pGlu-Trp-Ala-Gln-Phe-Lys-Ile-Gln-Trp-Asn-Gln-Arg-Trp-Gly-Arg-Arg | (SEQ ID NO: 20) |
| Glu/pGlu-Trp-Val-Gln-Phe-Lys-Ile-Gln-Trp-Asn-Gln-Arg-Trp-Gly-Arg-Arg | (SEQ ID NO: 21) |
| Glu/pGlu-Trp-Thr-Gln-Phe-Lys-Ile-Gln-Trp-Ser-Gln-Arg-Trp-Gly-Arg-Arg | (SEQ ID NO: 22) |
| Glu/pGlu-Trp-Ala-Gln-Phe-Lys-Ile-Gln-Trp-Ser-His-Arg-Trp-Gly-Arg-Arg | (SEQ ID NO: 23) |
| Lys-Arg-Gln-Trp-Ala-Gln-Phe-Lys-Ile-Gln-Trp-Asn-Gln-Arg-Trp-Gly-Arg-Arg | (SEQ ID NO: 24) |
| Lys-Arg-Gln-Trp-Val-Gln-Phe-Lys-Ile-Gln-Trp-Asn-Gln-Arg-Trp-Gly-Arg-Arg | (SEQ ID NO: 25) |
| Lys-Arg-Gln-Trp-Thr-Gln-Phe-Lys-Ile-Gln-Trp-Ser-Gln-Arg-Trp-Gly-Arg-Arg | (SEQ ID NO: 26) |
| Lys-Arg-Gln-Trp-Ala-Gln-Phe-Lys-Ile-Gln-Trp-Ser-His-Arg-Trp-Gly-Arg-Arg | (SEQ ID NO: 27) |

Given the present formulas, the present provisions, and examples such as those provided in Table 1, one of ordinary skill in the art is well able to select various substituted amino acid residues from among those permitted and to make and use peptides conforming to the present formulas and variants thereof.

The polypeptides of the invention can be characterized in terms of their similarity to a reference sequence. For example, the invention features substantially pure polypeptides that have, or that include, an amino acid sequence that is at least 60% identical to an amino acid sequence shown in Table 1 or otherwise described herein. For example, the polypeptide can be at least 60% identical to: Trp-Ala-Gln-Phe-Lys-Ile-Gln-Trp-Asn-Gln-Arg-Trp (SEQ ID NO:4). The polypeptide can differ from the reference sequence by virtue of substitution, deletion, or addition of at least one amino acid residue or by a combination of one or more substitutions, deletions, or additions. For example, the polypeptide can lack the carboxy-terminal Trp residue and may be otherwise configured as described herein. For example, the amino-terminal can be extended to include the amino acid triplet Lys-Arg-Gln. Polypeptides that consist of, or that include, an amino acid sequence that is at least 60% identical to a reference sequence (i.e., a portion of a CR, examples of which are shown herein) and that retain sufficient biological activity to positively impact bone are biologically active variants of a fragment of a CR.

In another aspect, the polypeptides of the invention can consist of, or include, a sequence conforming to the formula: $Xaa_1$-$Xaa_2$-$Xaa_3$-Trp-$Xaa_5$-Gln-$Xaa_7$-$Xaa_8$-$Xaa_9$-Gln-$Xaa_{11}$-$Xaa_{12}$-$Xaa_{13}$-Arg (III) (SEQ ID NO:34). Within Formula (III), $Xaa_1$ is Lys or is absent; $Xaa_2$ is Arg or is absent; $Xaa_3$ is Gln, pyroglutamate (pGln) or is absent; $Xaa_5$ is Ala, Val, Thr or Asn; $Xaa_7$ is Phe or Tyr; $Xaa_8$ is Lys or Gln; $Xaa_9$ is Ile or Ala; $Xaa_{10}$ is Trp or is absent; $Xaa_{12}$ is Asn, Ser or is absent; and $Xaa_{13}$ is Gln, His or is absent. The polypeptide can have, but is not limited to, 7-14 amino acid residues. As in other formulas presented herein, Xaa represents an amino acid, which we may also refer to as an amino acid residue. The subscripts (here, the subscripts 1-13) represent the positions of each amino acid in the peptide sequence. Thus, $Xaa_1$ represents the first amino acid residue in a polypeptide of the invention (with $Xaa_1$-$Xaa_3$ representing the optional trimer Lys-Arg-Gln. For example, a polypeptide of the invention can consist of, or can include, the amino acid sequence Lys-Arg-Gln-Trp-Ala-Gln-Phe-Lys-Ile-Gln-Trp-Asn-Gln-Arg (SEQ ID NO:35). Similarly, any of the polypeptides described herein can terminate at the arginine residue corresponding to the Arg at position 14 of SEQ ID NO:34 or 35. Where the CR-derived polypeptide terminates, the carboxy terminus may further include the amino acid triplet Gly-Arg-Arg.

The amino acid residues included in polypeptides of the invention can be of the D- or L-form or a combination thereof. Where the polypeptide is a biologically active variant of a fragment of a CR, the polypeptide can be a variant by virtue of including a non-naturally occurring amino acid residue. For example, a polypeptide of the invention can include one or more pGlu residues (e.g., at the amino terminus). The polypeptides can also include more than one CR-derived sequence. For example, the polypeptides can include two, three, or four tandem repeats of a CR-derived sequence (e.g., a sequence conforming to SEQ ID NO:4 and/or biologically active variants thereof). The polypeptides can be separated by a linker (e.g., a peptide linker that may be cleavable by a cellular enzyme).

The polypeptides of the invention can also include structural modifications that may, for example, enhance the therapeutic efficacy of the polypeptides or assist clinicians in monitoring a course of treatment with the polypeptides. Structural modifications can be made during or after polypeptide translation or chemical synthesis. For example, the polypeptides can be amidated. Alternatively, or in addition, the polypeptides can include a detectable marker. Both the form and position of the detectable marker can vary, as long as the polypeptides retain sufficient biological activity to remain useful. The marker can be, for example, a photoaffinity ligand, a radioisotope, or a fluorescent or chemiluminescent compound.

In addition to the polypeptides described herein, the invention features pharmaceutical formulations that include these polypeptides, nucleic acids that encode them, host cells that express them, and kits including one or more of these compositions. The nucleic acids, vectors containing them, and host cells can also be formulated as pharmaceutical preparations.

Methods for constructing nucleic acids that encode a given polypeptide are well known in the art. The nucleic acids that encode a fragment of a CR or a biologically active variant thereof include those that are codon optimized. For expression, the nucleic acids can readily be incorporated into a vector (e.g., a plasmid or viral vector), and such vectors are encompassed by the invention. The nucleic acids can be operably linked to a regulatory region suitable for use in either a prokaryotic or a eukaryotic system, many of which are known in the art and can be used to produce the polypeptides described herein. In specific embodiments, the regulatory region can be, for example, a promoter or enhancer. Useful promoters include cell type-specific promoters, tissue-specific promoters, constitutively active promoters, and broadly expressing promoters. As noted, host cells including vectors that express a polypeptide of the invention are also encompassed by the invention, and these cells can be prokaryotic (e.g., bacterial) or eukaryotic (e.g., mammalian).

The polypeptides, nucleic acids, vectors, and host cells of the invention can be formulated as pharmaceutical compositions. For example, these compositions can be formulated as non-toxic preparations for parenteral (e.g., intravenous) administration. The pharmaceutical compositions can include polypeptides of more than one sequence. For example, the pharmaceutical compositions can include a first polypeptide having a sequence that is identical to that of a fragment of a CR and a second polypeptide that is a biologically active variant thereof (e.g., a sequence including a pGln residue). In other words, the pharmaceutical formulations can include mixtures of polypeptides. As noted above, the polypeptides of the invention encompass those in which more than one of the CR-derived polypeptides of the invention is included within a longer polypeptide, and such multimers, whether assembled as fusion proteins or conjugates, can also be formulated for administration to a patient. Carriers and stabilizing agents may be added to facilitate drug delivery and to insure shelf-life. For example, encapsulation of the polypeptides in a suitable delivery vehicle (e.g., polymeric microparticles, implantable devices, or any configuration for timed-, delayed-, or controlled release) may increase the efficiency of delivery.

The methods of the invention include methods for treating a subject (e.g., a human patient) who has a compromised bone or bone tissue. The compromise may be due to a disorder, a term we use to encompass a disease or physiological condition of any sort that compromises bone, or to a traumatic injury, whether resulting from, for example, an accident or sporting injury, or whether induced intentionally, for example in the context of a surgical procedure. For example, the condition may have a genetic basis, may be related to a dietary problem, may result from or be associated with aging, or may result from or be associated with cancer or a benign growth. The cause may also be unknown. The disorder may be one that diminishes bone density. More specifically, patients amenable to treatment with the compositions described herein may have been diagnosed as having, or to be at risk for developing, osteoporosis, osteopenia, osteomalacia, Paget's disease of the bone, osteogenesis imperfecta, or renal osteodystrophy and osteonecrosis (also termed avascular necrosis, bone infarction, aseptic necrosis, and ischemic bone necrosis). As noted, other subjects may have a cancer (e.g., a tumor) or non-malignant growth (e.g., a bone cyst) that affects bone density. The cancer can be a bone cancer per se (i.e., a primary tumor that originates in the bone), such as osteosarcoma. The cancer can also be a secondary tumor that has metastasized to the bone from another site (e.g., a breast, lung, prostate, or kidney tumor). Thus, patients amenable to treatment include those who have cancer that may metastasize to the bone. As noted, bone may also be compromised by an injury, and the injury may be unintentional (i.e., accidental) or intentional (e.g., it may result from a surgical procedure on a bone). In other embodiments, directed to prophylactic use, the polypeptides of the invention (or nucleic acids encoding them) can be administered prophylactically to maintain bone (e.g., bone strength) as a patient ages. Any patient can be treated, but patients who are about or at least 50 years old are particular candidates. While the treatment methods of the invention, whether therapeutic or prophylactic, are suitable for human use, the invention is not so limited, and veterinary use is also encompassed.

The methods of the invention can include a step of identifying a subject who has or who is likely to develop compromised bone. Unless the context clearly indicates otherwise, we use the terms "subject" and "patient" interchangeably. Whether prophylactic or therapeutic, the methods involve administering to the subject a pharmaceutical composition as described herein. The active agent (e.g., the CR-derived polypeptide) will be present in a therapeutically effective amount, and the route of administration and regime can vary. It is understood in the art that the required dosage, dosing schedule, and length of treatment depend upon various factors typically considered by one of ordinary skill in the art. These factors include the route of administration, the nature of the formulation, the nature of the patient's illness, the subject's size, weight, surface area, age, gender, other drugs being administered to the patient, and the judgment of the attending physician. Suitable dosages are in the range of 0.01-100.0 µg/kg. Our in vitro cell culture studies show that effective concentrations in vitro range from about 2-15 µM. The compositions can be administered along with or in addition to another treatment for particular bone disorders (e.g., drug therapy, immobilization, surgery, or immunotherapy). While we believe we understand certain events that are likely to occur in the course of treatment, the compositions of the present invention are not limited to those that work by affecting any particular cellular mechanism.

In addition to prophylactic and therapeutic methods to, for example, maintain, repair, replace, strengthen, or fully or partially heal, restore, or improve the strength of a bone, the present invention features methods of making the polypeptides, nucleic acids, vectors, and transformed host cells described herein and methods of incorporating those agents into physiologically acceptable (e.g., pharmaceutically acceptable) compositions.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is a representation of the amino acid sequence of a human calcitonin receptor (SEQ ID NO:44). An exemplary polypeptide of the invention is underlined.

FIG. 2 is an alignment of polypeptides derived from calcitonin receptors of several mammals (rabbit, mouse, rat, pig, and human sequences are shown; SEQ ID Nos.:45-49, respectively, in order of appearance). Scrambled polypeptides (polypeptides having the same amino acids as the polypeptide derived from a human calcitonin receptor, but in a scrambled order), are also shown (SEQ ID Nos.:50 and 36-38, respectively, in order of appearance).

FIG. 3 is a panel of photomicrographs illustrating the effect of CRP on fracture healing as simulated in an osteoblast cell culture.

DETAILED DESCRIPTION

Figure 4:
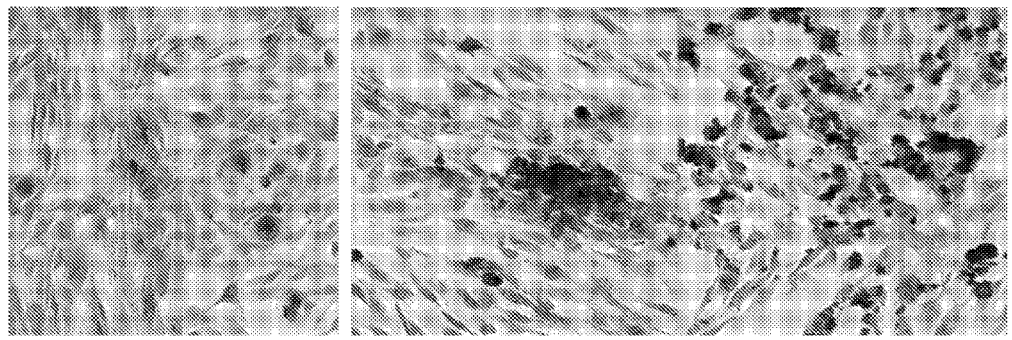
FIG. 4 is a panel of photomicrographs illustrating the effect of polypeptides of the present invention on the formation of bone matrix as simulated by treatment of hFOB cells in culture.

Bone matrix is a dense mixture composed mainly of collagen fibers and calcium phosphate particles, with a population of living cells contained within. Despite its rigidity, bone continually undergoes a remodeling process that requires the coordinated activity of two types of cells, osteoclasts and osteoblasts. Osteoclasts are related to macrophages, and erode the bone matrix by secreting acids and hydrolases to dissolve bone minerals and digest organic components. Osteoblasts arise from undifferentiated precursor cells, and deposit a mineralized matrix consisting of osteoid, where other minerals like calcium and phosphorus solidify the osteoid, leading to the formation of new bone. Osteoblasts have also been shown to express factors which regulate the differentiation and function of osteoclasts. The balance between the activity of osteoblasts and osteoclasts plays an important role in determining the mass and density of bone. Misregulation of osteoblasts and osteoclasts may be a contributing factor in many bone disorders including osteoporosis, in which bone mass is greatly reduced.

The calcitonin receptor (CR) is a seven-transmembrane spanning G-protein coupled receptor involved in the regulation of osteoclast-mediated bone resorption and in maintaining calcium homeostasis. The calcitonin receptor is the specific receptor for the peptide hormone calcitonin, and it has also been referred to in the art as CTR, CT-R, CRT, CTR1 and CALCR. Polymorphisms in the CR gene have been associated with variations in bone mineral density and the onset of osteoporosis. CR is expressed in a variety of cell types, including osteoclasts.

Bone disorders remain a major cause of morbidity. The chronic, progressive nature of many bone disorders can have a debilitating effect on every aspect of a person's daily life. In the elderly, bone disorders such as osteoporosis contribute to an increased risk of bone fractures that may significantly impact both the quality of life and life expectancy. For many individuals with bone disorders, the available remedies consist primarily of palliative care rather than curative treatments. There is a continuing need for therapeutic strategies that target bone formation and maintenance.

Disclosed herein are materials and methods related to the production and use of fragments of a CR and biologically active variants thereof for the treatment and management of bone, including aging and compromised bone.

Polypeptides:

We refer to the amino acid-based compositions of the invention as "polypeptides" to convey that they are linear polymers of amino acid residues, and to help distinguish them from full-length proteins. While the content of the polypeptides of the invention can vary, none of them are full-length, naturally-occurring CRs. We have stated that a polypeptide of the invention can "constitute" or "include" a fragment of a CR, and the invention encompasses polypeptides that constitute or include fragments of a CR or biologically active variants thereof. It will be understood that the polypeptides can therefore include only a fragment of a CR (or a biologically active variant thereof) but may include additional residues as well.

An amino acid sequence of a human calcitonin receptor, from which polypeptides of the invention can be derived, is shown in FIG. 1. Although the invention is not so limited, residues suitable for inclusion in a polypeptide of the invention are underlined (see also GenBank sequence NM_001164737.1 public GI:260064023). Other useful and representative forms of CR are known in the art (see, e.g., NP_001158209.1 public GI:260064024; NM_001164738.1 public GI:260064026; NP_001158210.1; public GI:260064027; NM_001742.3; public GI:260064022; NP_001733.1; public GI:4502547). For example, the polypeptides of the invention can be derived from a homolog or ortholog of a human CR (see FIG. 2), and polypeptides of these forms are encompassed by the present invention.

The polypeptides of the invention can vary in length. For example, the polypeptides can be 8-40 (e.g., 12, 14, 16, 18, or 20) amino acids long or longer (e.g., up to about 40 residues).

More specifically, in one aspect, the polypeptide of the invention is, or includes, a fragment of a calcitonin receptor or a biologically active variant of such a fragment, the amino acid sequence of the polypeptide conforming to Formula (I):

(SEQ ID NO: 1)
Trp-Xaa$_2$-Gln-Xaa$_4$-Xaa$_5$-Xaa$_6$-Gln-Trp-Xaa$_9$-

Xaa$_{10}$-Arg-Trp (I).

In Formula (I), Xaa$_2$ is Ala, Val, Thr, or Asn; Xaa$_4$ is Phe or Tyr; Xaa$_5$ is Lys or Gln; Xaa$_6$ is Ile or Ala; Xaa$_9$ is Asn or Ser; and Xaa$_{10}$ is Gln or His. In particular embodiments, Xaa$_2$ can be Ala; Xaa$_4$ can be Phe; Xaa$_5$ can be Lys; Xaa$_6$ can be Ile; Xaa$_9$ can be Asn; and Xaa$_{10}$ can be Gln. These residues can be selected independently of one another or in view of one another. In these embodiments and any others described herein, the polypeptide can be substantially pure.

A polypeptide of the invention can conform to Formula (I) and can further include at least one additional glutamate (Glu) or pyroglutamate (pGlu) residue at the amino terminus of the polypeptide. A polypeptide of the invention can include the amino acid triplet Lys-Arg-Gln at the amino terminus of the polypeptide. In that event, the amino acid sequence of the polypeptide would conform to: Lys-Arg-Gln-Trp-Xaa$_2$-Gln-Xaa$_4$-Xaa$_5$-Xaa$_6$-Gln-Trp-Xaa$_9$-Xaa$_{10}$-Arg-Trp (SEQ ID NO:2), with the unspecified residues selected from those listed above. The carboxy terminal may also be extended. For example, the carboxy terminal of the polypeptide can further include the amino acid triplet Gly-Arg-Arg. In that event the amino acid sequence of the polypeptide would conform to: Trp-Xaa$_2$-Gln-Xaa$_4$-Xaa$_5$-Xaa$_6$-Gln-Trp-Xaa$_9$-Xaa$_{10}$-Arg-Trp-Gly-Arg-Arg (SEQ ID NO:3). In these embodiments and any others described herein, the carboxy terminus of the polypeptide can be amidated.

In order to accommodate longer polypeptides, we derived Formula (II). Accordingly, the polypeptides of the invention can have, or can include, a sequence of amino acid residues conforming to Formula (II):

(SEQ ID NO: 28)
Xaa$_1$-Xaa$_2$-Xaa$_3$-Trp-Xaa$_5$-Gln-Xaa$_7$-Xaa$_8$-Xaa$_9$-

Gln-Xaa$_{11}$-Xaa$_{12}$-Xaa$_{13}$-Arg-Trp-Xaa$_{16}$-Gly-

Xaa$_{18}$- Xaa$_{19}$ (II).

Within Formula (II), Xaa$_1$ is Lys or is absent; Xaa$_2$ is Arg or is absent; Xaa$_3$ is Gln, pyroglutamate (pGlu) or is absent; Xaa$_5$ is Ala, Val, Thr or Asn; Xaa$_7$ is Phe or Tyr; Xaa$_8$ is Lys or Gln; Xaa$_9$ is Ile or Ala; Xaa$_{11}$ is Trp or is absent; Xaa$_{12}$ is Asn, Ser or is absent; Xaa$_{13}$ is Gln, His or is absent; Xaa$_{16}$ is Ala or is absent; Xaa$_{17}$ is Gly or is absent; Xaa$_{18}$ is Arg or is absent; and Xaa$_{19}$ is Arg or is absent. Xaa represents an amino acid, which we may also refer to as an amino acid residue. The subscripts (here, the subscripts 1-19) represent the positions of each amino acid in the peptide sequence. Thus, Xaa$_1$ represents the first amino acid residue in a polypeptide of the invention. To produce biologically active variants of the polypeptides of Formula II, one can truncate the polypeptide following the Arg residue at position 14 (between Arg and Trp).

In addition to the polypeptides shown in Table 1, the invention encompasses the following polypeptides, which were derived from a porcine CR and conform to Formula (II):

Lys-Arg-Gln-Trp-Asn-Gln-Tyr-Gln-Ala-Gln-Arg-Trp-Ala-Gly-Arg-Arg (SEQ ID NO:29);

Glu/pGlu-Trp-Asn-Gln-Tyr-Gln-Ala-Gln-Arg-Trp-Ala (SEQ ID NO:30);

Trp-Asn-Gln-Tyr-Gln-Ala-Gln-Arg-Trp-Ala (SEQ ID NO:31);

Trp-Asn-Gln-Tyr-Gln-Ala-Gln-Arg-Trp-Ala-Gly-Arg-Arg (SEQ ID NO:32); and

Glu/pGlu-Trp-Asn-Gln-Tyr-Gln-Ala-Gln-Arg-Trp-Ala-Gly-Arg-Arg (SEQ ID NO:33). To generate biologically active variants of these polypeptides, SEQ ID NO:30 can be terminated after the Arg residue at position 9; SEQ ID NO:31 can be terminated after the Arg residue at position 8; SEQ ID NO:32 can be terminated after the Arg residue at position 12; and SEQ ID NO:33 can be terminated after the Arg residue at position 13.

In another aspect, the polypeptides of the invention can consist of, or include, a sequence conforming to the formula:

Xaa$_1$-Xaa$_2$-Xaa$_3$-Trp-Xaa$_5$-Gln-Xaa$_7$-Xaa$_8$-Xaa$_9$-Gln-Xaa$_{11}$-Xaa$_{12}$-Xaa$_{13}$-Arg (III) (SEQ ID NO:34). Within Formula (III), Xaa$_1$ is Lys or is absent; Xaa$_2$ is Arg or is absent; Xaa$_3$ is Gln, pyroglutamate (pGlu) or is absent; Xaa$_5$ is Ala, Val, Thr or Asn; Xaa$_7$ is Phe or Tyr; Xaa$_8$ is Lys or Gln; Xaa$_9$ is Ile or Ala; Xaa$_{11}$ is Trp or is absent; Xaa$_{12}$ is Asn, Ser or is absent; and Xaa$_{13}$ is Gln, His or is absent. The polypeptide can have, but is not limited to, 7-14 amino acid residues.

In the formulas, amino acid residues are represented by the standard three-letter code. Where a variety of residues may be used, the amino acid is represented by Xaa, and the subscript represents the position of each amino acid in the generic formula. Other variant sequences, not specifically listed here, will be readily apparent, given the present formulas, provisions, and examples, to one of ordinary skill in the art.

For the sake of added clarity, the polypeptides of the invention exclude naturally occurring full-length CRs, but such full-length CRs may be included in the pharmaceutical compositions described herein, modified as described herein (e.g., amidated), and used together with the presently described polypeptides in any method or embodiment of the present invention.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a fragment of a CR can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

A particularly suitable post-translational modification for the present polypeptides is amidation. For example, the C-terminal residue can include an amino group. In vivo, amidation typically occurs at internal glycine residues and requires the sequential actions of three enzymes: two proteases ("paired basics"-specific endopetidase (e.g., prohormone convertase I) and carboxypetidase H) that cleave the precursor at the glycine residues and the amidating enzyme, peptidylglycine amidating monooxygenase (PAM). PAM catalyzes amide formation by hydroxylation of the glycine residue; the hydroxyglycine derivative dissociates to form a peptide that includes a C-terminal amide and glyoxylic acid. Methods for chemical synthesis of peptides amidated at the C-terminus are well known in the art. The synthesis can be carried out in solution or by solid-phase peptide synthetic techniques. Specific solid-phase methods for generating the amide group include, for example, without limitation, acidolysis of a benzhydral amide linkage between the peptide and the solid-support and ammonolysis of a peptide-resin ester linkage.

One or more of the amino acid residues in a biologically active variant may be a non-naturally occurring amino acid residue. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid. For other examples, one can consult textbooks or the worldwide web (for example, a site is currently maintained by the California institute of Technology and displays structures of non-natural amino acids that have been successfully incorporated into functional proteins). Non-natural amino acid residues and amino acid derivatives listed in U.S. Application No. 20040204561 (see ¶ 0042, for example) can also be used. Alternatively, or in addition, one or more of the amino acid residues in a biologically active variant can be a naturally occurring residue that differs from the naturally occurring residue found in the corresponding position in a wild type CR sequence. In other words, biologically active variants can include one or more amino acid substitutions, and these may be substitutions with naturally or non-naturally occurring residues (or a combination thereof). We may refer to a substitution, addition, or deletion of amino acid residues as a mutation of the wild type sequence. As noted, the substitution can replace a naturally occurring amino acid residue with a non-naturally occurring residue or just a different naturally occurring residue. Further the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of a CR can be characterized in terms of the extent to which their sequence is similar to or identical to the corresponding fragment of the CR. For example, the sequence of a biologically active variant can be at least or about 60% identical to corresponding residues in a wild type CR. For example, a biologically active variant of a CR polypeptide can have an amino acid sequence with at least or about 60% sequence identity (e.g., at least or about 65%, 70%, 75%, 80%, 85%, 90%, 95%, 97%, 98%, or 99% sequence identity) to a CR protein (e.g., to the amino acid sequence set forth in SEQ ID NO:4 or to another polypeptide as described herein (e.g., a polypeptide shown in Table 1 or represented by, for example, SEQ ID NOs:29-34 and 39-41) or to a homolog or ortholog thereof).

A biologically active variant of a CR polypeptide will retain sufficient biological activity to be useful in the present methods. The biological activity can be assessed in ways known to one of ordinary skill in the art and includes, without limitation, inhibition of bone resorption by osteoclasts, enhancement of calcium excretion, regulation of calcium homeostasis, G-protein activation and interaction with receptor activity-modifying proteins (RAMPs) forming the multimeric amylin receptors $AMY_1$ (CT+RAMP1), $AMY_2$ (CT+RAMP2), and $AMY_3$ (CT+RAMP3).

Biologically active variants can be identified, for example, by comparing the relative activities of the variant polypeptide with that of an active fragment of a CR. The assays can include an unrelated control polypeptide (e.g., one could include in any given assay a peptide that has the same amino acid content randomly arranged; see also the vehicle-only and other controls referenced in the Examples). Some biologically active variants may even have greater biological activity than the cognate, naturally occurring fragment or a full-length CR. More specifically, a biologically active variant can have at least or about 30%, 40%, 50%, 60%, 70%, 80%, 90%, 95%, 98%, or more of the biological activity of the native form polypeptide.

The methods that can be used to assess activity include in silico analyses, in vitro assays, cell-based assays and whole animal, in vivo, model systems. These assays can be configured to test the effect of any given fragment of a CR, or a variant thereof, on processes such as calcium mobilization, G-protein activation (e.g., GTP binding to Gs-alpha), bone matrix deposition and expression of genes in signal transduction pathways relating to bone matrix production.

Useful cell-based assays include those that examine activation of the G-protein coupled receptor complexes for CR. The complexes include 1) the Gs-alpha subunit of the heterotrimeric G protein subunit that activates the cAMP-dependent pathway by activating adenylate cyclase and 2) Gq, a heterotrimeric G protein subunit that activates phospholipase C (PLC). PLC in turn hydrolyzes phosphatidylinositol 4,5-bisphosphate ($PIP_2$) to diacyl glycerol (DAG) and inositol triphosphate ($IP_3$) signal transduction pathway. DAG acts as a second messenger that activates protein kinase C (PKC) and $IP_3$ helps in phosphorylation of some proteins. G-protein coupled receptors convert the peptide-receptor recognition signal into a small number of different "second messengers" (e.g., calcium fluxes across membranes, cyclic nucleotides, and phosphoinositides). Thus, modulation in the level or activity of one or more second messengers in polypeptide-treated cells relative to the corresponding levels in control (e.g., untreated) cells can be indicative of activation of the G-protein coupled receptor complex for CR, and assessing CR, fragments of a CR protein, and variants thereof indicates the relative levels of biological activity each agent possesses.

Assessing second messenger activity is routine in the art, and kits and reagents for performing such assays are readily available from commercial sources. For example, alterations in calcium levels can be assayed with calcium-sensitive dyes such as Calcium Crimson-AM (Invitrogen, Carlsbad, Calif.), FLIPR (Molecular Devices, Sunnyvale, Calif.), Fluo4 and Fura Red (Caliper Life Sciences, Hopkinton, Mass.), which can be monitored either by microscopy or fluorometry. Modulation of cyclic nucleotides can be assayed by chemiluminescence, immunoassays, or fluorescence polarization techniques. Changes in phosphoinositide levels can be evaluated by fluorescence polarization, immunoassays and other downstream markers such as D-myo-inositol 1-phosphate.

Peptide activity can also be monitored in cell-based assays that measure the impact of a given polypeptide (whether it is a fragment of a CR or a variant thereof) on specific cell functions (e.g., bone matrix production, or the signaling pathways involved in cell functions). Methods of measuring various bone matrix production are well-known in the art. In the context of the present invention, suitable assays include, for example, assays that measure calcium concentration using Alizarin Red S staining and von Kossa staining. Methods of analyzing signaling pathways are also well-known in the art and include, for example, RT-PCR analysis, gene arrays, immunoblotting, ELISA assays, Multidimensional Protein Identification Technology (MudPIT). Such analysis can involve a single gene, or multiple genes. Exemplary genes include but are not limited to calcitonin, osteonectin, osteopontin, Wnt, bone morphogenetic proteins (BMP), parathyroid hormone (PTH) or cytokines.

Any cell type that is responsive to a polypeptide of the invention, or any tissue containing such responsive cells, can be used to assess biological activity, including cell lines and explants. Particularly useful cell lines include the differentiating pre-osteoblast cell line, MC3T3-E1 and the immortalized human fetal osteoblast cell line, hFOB 1.19. Cell lines can be obtained from standard commercial sources and from depositories such as The American Type Culture Collection.

The present polypeptides can also be evaluated in vivo. Model animal systems for osteoporosis include sheep, rabbits and rats (e.g., the ovariectomized rat). Model systems for fractures include the rat femur fracture model. Such model animals can be treated with a polypeptide of the invention and screened (e.g., radiologically). In addition, tissue samples can be removed and analyzed by von Kossa staining and/or immunocytochemistry with antibodies to proteins involved in bone matrix production (e.g., osteocalcin, osteonectin, osteopontin, collagen, Wnt, or BMP).

The polypeptides of the invention can be chemically synthesized, obtained from natural sources (insofar as they constitute fragments of a naturally occurring CR), or purified from cells in which they are recombinantly produced. Of course, molecular techniques can be used to express polypeptides having a sequence that is identical to a portion of a CR or biologically active variants thereof; the methods required for polypeptide synthesis, expression and purification are well known in the art. For example, polypeptides can be chemically synthesized using standard f-moc chemistry and purified using high pressure liquid chromatography (HPLC). Fragments of a CR and biologically active variants thereof can be purified by any method known in the art, including without limitation, fractionation, centrifugation, and chromatography (e.g., gel filtration, ion exchange chromatography, reverse-phase HPLC and immunoaffinity purification).

The polypeptides may be, but are not necessarily, substantially pure. A polypeptide of the invention, whether it contains a sequence that is identical to a portion of a CR or a biologically active variant thereof, should be considered substantially pure when it has been separated from a substantial amount of the material with which it was previously associated (e.g., cellular components where the polypeptide is recombinantly produced or reagents where the polypeptide is chemically synthesized). For example, a polypeptide of the invention is substantially pure when it is present in a composition in which it constitutes at least or about 60% of the composition by weight (e.g., at least or about 65%, 70%, 80%, 90%, 95%, or 99%). If tested by electrophoresis, a substantially pure polypeptide will yield a single major band on a non-reducing polyacrylamide gel.

To produce a recombinant polypeptide of the invention, a nucleic acid sequence encoding the polypeptide can be incorporated into (e.g., ligated into) an expression vector and used to transform a prokaryotic cell (e.g., a bacterial cell) or transfect a eukaryotic host cell (e.g., an insect, yeast, or mammalian host cell). In general, nucleic acid constructs can include one or more regulatory sequences operably linked to a nucleic acid sequence encoding a polypeptide of the invention. Regulatory sequences (e.g., promoters, enhancers, polyadenylation signals, and terminators) do not typically encode a protein/polypeptide, but instead affect the expression of a nucleic acid sequence. Such transformed or transfected cells can then be used, for example, for large or small scale production of the selected fragment of a CR (or a biologically active variant thereof) by methods known in the art. In essence, such methods involve culturing the cells under conditions suitable for production of the polypeptide and isolating the polypeptide from the cells or from the culture medium.

A construct can include a tag sequence designed to facilitate subsequent manipulations of the expressed nucleic acid sequence. For example, the tag can facilitate purification or localization. Tag sequences, such as green fluorescent protein (GFP), glutathione S-transferase (GST), c-myc, hemagglutinin, β-galactosidase, or Flag™ tag (Kodak) sequences are typically expressed as a fusion with the polypeptide encoded by the nucleic acid sequence. Such tags can be inserted in a nucleic acid sequence such that they are expressed anywhere along an encoded polypeptide including, for example, at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include, without limitation, pBAD (Invitrogen, Carlsbad, Calif.), the pTYB family of vectors (New England Biolabs), and pGEMEX vectors (Promega); representative mammalian expression vectors include, without limitation, pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include, without limitation, pBacPAK8 or pBacPAK9 (Clontech), and p2Bac (Invitrogen); and representative yeast expression vectors include, without limitation, MATCHMAKER (Clontech) and pPICZ A, B, and C (Invitrogen).

In bacterial systems, *Escherichia coli* can be used to express a fragment of a CR or a biologically active variant thereof. For example, the *E. coli* strain DH10B (Invitrogen) can be transformed with the gram negative broad host range vector, pCM66 containing a nucleic acid sequence encoding a fragment of a CR protein. In another example, BL-21 cells can be transformed with a pGEX vector containing a nucleic acid sequence encoding a polypeptide of the invention. The transformed bacteria can be grown exponentially and then stimulated with isopropylthiogalactopyranoside (IPTG) prior to harvesting. In general, the polypeptides produced from a pGEX expression vector can be purified from lysed cells by adsorption to glutathione-agarose beads followed by elution in the presence of free glutathione. The pGEX vectors can be designed to include thrombin or factor Xa protease cleavage sites so that the expressed polypeptide can be released from the GST moiety.

The invention further encompasses peptidomimetics of fragments of a CR, which are small, protein-like polymers containing non-peptidic structural elements that are capable of mimicking or antagonizing the biological actions of a natural parent peptide (here, a fragment of a CR or a biologically active variant thereof). In addition to being synthetic, non-peptide compounds, peptidomimetics can have a three-dimensional conformation (i.e., a "peptide motif") that is substantially the same as the three-dimensional conformation of a selected polypeptide. The peptide motif provides the peptidomimetic compound with the ability to bind the receptor in a manner qualitatively identical to that of the parent peptide from which the peptidomimetic was derived. Peptidomimetic compounds can have additional characteristics that enhance their therapeutic utility, such as an increased biological half-life.

The peptidomimetics typically have a backbone that is partially or completely non-peptide, but with side groups that are identical to the side groups of the amino acid residues that occur in the peptide on which the peptidomimetic is based. Several types of chemical bonds (e.g., ester, thioester, thioamide, retroamide, reduced carbonyl, dimethylene and ketomethylene bonds) are known in the art to be generally useful substitutes for peptide bonds in the construction of protease-resistant peptidomimetics and can be used in the context of the present peptides).

Any peptidomimetic that has a sufficient amount of biological activity (e.g., an amount that renders the peptidomimetic experimentally or clinically useful) can be used.

As noted above in describing suitable expression vectors, the present polypeptides can include a tag, which may also be referred to as a reporter or marker (e.g., a detectable marker). A detectable marker can be any molecule that is covalently linked to the fragment of a CR or a biologically active fragment thereof that allows for qualitative and/or quantitative assessment of the expression or activity of the tagged peptide. The activity can include a biological activity, a physico-chemical activity, or a combination thereof. Both the form and position of the detectable marker can vary, as long as the labeled peptide retains biological activity. Many different markers can be used, and the choice of a particular marker will depend upon the desired application. Labeled polypeptides can be used, for example, for evaluating the phamacokinetics of the polypeptide both in cell-based systems and in whole animal models.

Suitable markers include, for example, enzymes, photo-affinity ligands, radioisotopes, and fluorescent or chemiluminescent compounds. Methods of introducing detectable markers into peptides are well known in the art. Markers can be added during synthesis or post-synthetically. Recombinant polypeptides can also be labeled by the addition of labeled precursors (e.g., radiolabeled amino acids) to the culture medium in which the transformed cells are grown. In some embodiments, analogues or variants of the polypeptides of the invention can be used in order to facilitate incorporation of detectable markers. For example, any N-terminal phenylalanine residue can be replaced with a closely related aromatic amino acid, such as tyrosine, that can be easily labeled with $^{125}$I. In some embodiments, additional functional groups that support effective labeling can be added to the polypeptides. For example, a 3-tributyltinbenzoyl group can be added to the N-terminus of the native structure; subsequent displacement of the tributyltin group with $^{125}$I will generate a radiolabeled iodobenzoyl group.

Nucleic Acids:

We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a naturally occurring CR or a biologically active variant thereof.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein (i.e. a fragment of a CR protein or a biologically active variant thereof). PCR can be used to amplify specific sequences from DNA as well as RNA, including sequences from total genomic DNA or total cellular RNA. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid (as one may wish to do, for example, when making a biologically active variant of a fragment of a CR protein).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of a CR-encoding DNA (in accordance with, for example, the formula above).

Two nucleic acids or the polypeptides they encode may be described as having a certain degree of identity to one another. For example, a fragment of a CR protein and a biologically active variant thereof may be described as exhibiting a certain degree of identity. Alignments may be assembled by locating short CR sequence in the Protein Information Research (PIR) site (pir.georgetown.edu), followed by analysis with the "short nearly identical sequences" Basic Local Alignment Search Tool (BLAST) algorithm on the NCBI website (ncbi.nlm.nih.gov/blast).

As used herein, the term "percent sequence identity" refers to the degree of identity between any given query sequence and a subject sequence. For example, a naturally occurring CR can be the query sequence and a fragment of a CR protein can be the subject sequence. Similarly, a fragment of a CR protein can be the query sequence and a biologically active variant thereof can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., *Nucleic Acids Res.* 31:3497-3500, 2003.

ClustalW calculates the best match between a query and one or more subject sequences and aligns them so that identities, similarities and differences can be determined. Gaps of one or more residues can be inserted into a query sequence, a subject sequence, or both, to maximize sequence alignments. For fast pair wise alignment of nucleic acid sequences, the following default parameters are used: word size: 2; window size: 4; scoring method: percentage; number of top diagonals: 4; and gap penalty: 5. For multiple alignments of nucleic acid sequences, the following parameters are used: gap opening penalty: 10.0; gap extension penalty: 5.0; and weight transitions: yes. For fast pair wise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express fragments of a CR protein. A recombinant nucleic acid construct comprises a nucleic acid encoding a fragment of a CR protein as described herein, operably linked to a regulatory region suitable for expressing the fragment of a CR protein in the cell. Thus, a nucleic acid can comprise a coding sequence that encodes any of the fragments of a CR protein as set forth in, for example, in SEQ ID NO:4 or another polypeptide as described herein (e.g., a polypeptide shown in Table 1 or represented by, for example, SEQ ID NOs:29-34 or 39-41, or to homolog or ortholog thereof). In some cases, a recombinant nucleic acid construct can include a nucleic acid comprising a coding sequence, a gene, or a fragment of a coding sequence or gene in an antisense orientation so that the antisense strand of RNA is transcribed. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for a given fragment of a CR protein can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Pharmaceutical Formulations:

The polypeptides, nucleic acids (including vector constructs), and host cells of the invention can be formulated as stock solutions (suitable for storage and dilution) or as pharmaceutical formulations (suitable for administration to a patient).

The pharmaceutical formulations can include agents known in the art, including one or more physiologically acceptable carriers, excipients, or diluents. Further, the formulations can be made according to known methods for preparing peptide-based therapeutics for administration (e.g., by intravenous, intramuscular, subcutaneous, or intraperitoneal injection).

Methods of Treatment:

The polypeptides, nucleic acids (including vector constructs), and host cells of the invention are useful in treating patients who are at risk of, or who have been diagnosed as having, a compromised bone.

Treatment can completely or partially abolish some or all of the signs and symptoms of the bone disorder, decrease the severity of the symptoms, delay their onset, or lessen the progression or severity of subsequently developed symptoms.

Bone disorders that can be treated with the peptides described herein include those in which bone density is diminished. These disorders may be the result of disease or of an unknown cause, and they may be influenced by one's genetic constitution. Diminished bone density is a common underlying feature of many bone disorders. A patient who has a bone disorder associated with diminished bone density is a candidate for treatment with the present polypeptides. In some instances, it may be determined that administering a nucleic acid encoding a polypeptide of the invention is a preferred means of treatment or of reducing a subject's risk of developing a bone disorder.

Bone disorders include osteoporosis, osteopenia, osteomalacia, Paget's disease of the bone, osteogenesis imperfecta, or renal osteodystrophy and osteonecrosis (also termed avascular necrosis, bone infarction, aseptic necrosis, and ischemic bone necrosis). Other bone disorders can also include tumors that affect bone density, for example, primary tumors that originate in bone, whether malignant or non-malignant (e.g., bone cysts, chondrosarcomas, and osteosarcomas) or tumors that have metastasized to bone tissue (e.g. tumors that have metastasized from the breast, prostate, kidney, or other non-bone tumor). As noted, other patients amenable to treatment include those who have experienced a physical trauma that damages the osseous tissue. For example, a subject may have a bone fracture or any other condition in which there is a break in the continuity of the bone. In some instances, a physical injury can be the result of a metabolic condition or disease process (e.g., osteoporosis or a bone tumor).

Administration and Formulation:

Fragments of a calcitonin receptor and biologically active variants thereof can be administered directly to a mammal. Generally, the polypeptides can be suspended in a pharmaceutically acceptable carrier (e.g., physiological saline or a buffered saline solution) to facilitate their delivery. Encapsulation of the polypeptides in a suitable delivery vehicle (e.g., polymeric microparticles or implantable devices) may increase the efficiency of delivery. A composition can be made by combining any of the peptides provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present. It will be appreciated that any material described herein that is to be administered to a mammal can contain one or more pharmaceutically acceptable carriers.

Any composition described herein can be administered to any part of the host's body for subsequent delivery to a calcitonin receptor protein responsive cell. A composition can be delivered to, without limitation, the bones, bone marrow, joints, nasal mucosa, blood, lungs, intestines, muscle tissues, skin, or the peritoneal cavity of a mammal. In terms of routes of delivery, a composition can be administered by intravenous, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinician. Suitable dosages are in the range of 0.01-1,000 µg/kg Wide variations in the needed dosage are to be expected in view of the variety of fragments of a calcitonin receptor protein and biologically active variants available and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the fragments of a calcitonin receptor protein in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, fragments of a calcitonin receptor protein and biologically active variants thereof can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present peptides can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to one of ordinary skill in the art can be used to determine if a particular response is induced. Clinical methods that can assess the degree of a particular disease state can be used to determine if a response is induced. For example, in an osteoporosis patient, bone density measurements using standard methods (e.g., dual-energy x-ray absorption (DEXA), quantitative CT-scans, or quantitative ultrasound of the heel) can be used to assess bone density. For some disorders, blood or laboratory tests can be used to assist the clinician in evaluating a patient's response to a polypeptide of the invention. Exemplary tests include, for example, measurements of serum calcium levels, PTH levels, thyroid-stimulating hormone levels, and serum alkaline phosphatase levels. The particular methods used to evaluate a response will depend upon the nature of the patient's disorder, the patient's age, and sex, other drugs being administered, and the judgment of the attending clinician.

Alternatively, a polynucleotide containing a nucleic acid sequence encoding a fragment of a CR or a biologically active fragment thereof can be delivered to an appropriate cell of the subject. This can be achieved by, for example, the use of a polymeric, biodegradable microparticle or microcapsule delivery vehicle, sized to optimize phagocytosis by phagocytic cells such as macrophages. For example, PLGA (poly-lactide-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 µm and preferably larger than 20 µm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the fragment of a CRP protein of interest (or the biologically active variant thereof) with an initiator methionine and optionally a targeting sequence is operatively linked to a promoter or enhancer-promoter combination. Promoters and enhancers are described above, and many are well known in the art.

Polynucleotides can be administered in a pharmaceutically acceptable carrier. Pharmaceutically acceptable carriers are biologically compatible vehicles which are suitable for administration to a human or other mammalian subject (e.g., physiological saline). A therapeutically effective amount is an amount of the polynucleotide which is capable of producing a medically desirable result (e.g., a decrease in clinical motor symptoms) in a treated mammal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

As noted, the present formulations encompass mixtures of the polypeptides of the invention, and the formulations can include a combination of peptides of 2, 3, 4, 5, 6, 7, 8, 9, 10, 15, 20, 30, or more different amino acid sequences. The formulation can also include a mixture of polypeptides based on post-synthetic modified (e.g., amidation) or other post-translational modifications. Where nucleic acids are formulated as pharmaceutical compositions, the nucleic acids can similarly encode polypeptides in the configurations just described.

The polypeptides provided herein can be administered in conjunction with other therapeutic modalities to an individual in need of therapy. The present polypeptides can be given prior to, simultaneously with or after treatment with other agents or regimes. For example, the polypeptides can be administered in conjunction with other therapies for treating bone disorders, such as standard, small molecule-type pharmaceutical agents, biopharmaceuticals (e.g., antibodies or antibody-related immunotherapies, siRNAs, shRNAs, antisense oligonucleotides and other RNA inhibitory molecules, microRNAs, and peptide therapeutics), surgery, or in conjunction with any medical devices that may be used to assist the patient. Standard therapies for treating bone density disorders such as osteoporosis can include, for example, bisphosphonates, salmon calcitonin, estrogen, PTH and SERMs (selective estrogen receptor modulators, e.g., Raloxifene®).

The polypeptides can also be administered in conjunction with orthopedic supports, analgesics, heat, massage, orthopedic garments and exercise programs. In some cases, vertebroplasty, sometimes preceded by kyphoplasty, can relieve severe pain. In vertebroplasty, methyl methacrylate is injected into the vertebral body. In kyphoplasty, the vertebral body is expanded with a balloon.

Kits:

The compositions described herein can also be assembled in kits, together with instructions for use. For example, the kits can include measured amounts of a pharmaceutically acceptable composition including fragments of a CR protein and/or biologically active variants thereof. The instructions for use can be conveyed by any suitable media. For example, they can be printed on a paper insert in one or more languages or supplied audibly or visually (e.g., on a compact disc). The packaging materials can include vials, packets, or intravenous bags, and the kit can also include instruments useful in administration, such as needles, syringes, tubing, catheters, bandages, and tape. Preferably, the components of the kit are sterile and suitable for immediate use. The invention encompasses kits, however, that include concentrated formulations and/or materials that may require reconstitution, dilution, sterilization, or some other preparatory step prior to use.

EXAMPLES

Example 1

Identification of Calcitonin Receptor-Derived Polypeptides

We identified a calcitonin receptor-derived polypeptide (CRP) using an algorithm designed to define precursors of pyroglutamylpeptide amides. The CRP amino acid sequence corresponded to the highly conserved G-protein interaction site in the C terminal region of a human calcitonin receptor, and the polypeptides of the invention may be characterized as including the sequence of such an interaction sites. The amino acid sequence of a human calcitonin receptor is shown in FIG. 1, and the location of a CRP sequence is underlined.

Homologous sequences from other species were then identified using the "short nearly identical sequences" Basic Local Alignment Search Tool (BLAST) algorithm on the NCBI website (www.ncbi.nlm.nih.gov/blast) and the Protein Information Research (PIR) site (www.pir.georgetown.edu). Amino acid sequence alignments of the CRP homologues from rabbit (SEQ ID NO:45), mouse (SEQ ID NO:46), rat (SEQ ID NO:47) and pig (SEQ ID NO:48) are shown in FIG. 2.

Example 2

Effect of CRP on $Ca^{2+}$ Release and GTP Binding in PC12 Cells

We evaluated the effect of CRP on $Ca^{2+}$ mobilization by calcium green fluorescence monitoring in PC12 (rat adrenal pheochromocytoma) cells. CRP was synthesized with an N-terminal pyroglutamate (pGlu) moiety and an amidated C-terminal end.

CRP peptide was synthesized by conventional methods with an N-terminal pyroglutamate and an amidated C-terminal. The cells were treated with increasing concentrations of CRP (33 µM, 66 µM, 99 µM, 132 µM and 165 µM) in 50% DMSO. Negative control cells were treated with DMSO alone, and positive control cells were treated with 1 µM bradykinin. The rise in internal calcium was monitored as the change in fluorescence units. The CRP-treated cells showed a strong dose-dependent calcium mobilization response. No effect was seen with unamidated CRP (i.e., CRP having a carboxylic acid C-terminal) suggesting that only the amidated peptide was bioactive.

We also asked whether the rise in intracellular calcium was derived from internal calcium stores or an influx of extracellular calcium. PC12 cells were treated with CRP as above in the presence and absence of extracellular calcium. The increase in intracellular calcium was virtually identical in CRP-treated cells grown in the presence or absence of calcium, suggesting that the increase in intracellular calcium was due to release of calcium from internal stores.

These data suggested that CRP acted via G-protein associated transmembrane receptors. The ability of CRP to activate G-protein associated transmembrane receptors was assayed directly. Briefly, purified G-protein alpha subunits were treated with increasing concentrations of CRP (0.05, 0.1, 0.15, 0.2). CRP treated G-protein subunits showed a significant dose-dependent increase in GTP binding relative to DMSO-treated subunits.

Example 3

Effect of CRP on Bone Matrix Production in Differentiating Cells

The effect of CRP on bone matrix production was assayed in the chondrocyte preosteoblast cell line, MC3T3-E1. The cells were differentiated according to the method provided with the Millipore Osteogenesis kit and then treated with CRP at 1 or 10 µM for 48 hours. Bone matrix deposition was assayed according to the Alizarin Red S staining method provided with the Millipore Osteogenesis Quantitation kit. Relative to a standard curve generated using Alizarin dye, CRP-treated cells showed a dose-dependent increase in Alizarin Red-detectable calcium indicating a four to fivefold increase in bone matrix deposition. CRP increased the production of bone matrix in both differentiating and terminally differentiated cells.

Example 4

Effect of CRP on Bone Matrix Production in Differentiated Osteoblasts

The effect of CRP on differentiated osteoblasts was analyzed in an immortalized human fetal osteoblast cell line, hFOB 1.19. hFOB cells were incubated for 48 hours in increasing concentrations of CRP (4.6 µM, 9.2 µM, 13.8 µM and 18.4 µM). Bone matrix formation was assayed using a Millipore Osteogenesis Quantitation kit as described above. Phase contrast and fluorescent images of the Alizarin Red stained cells were acquired using an Olympus-IMT microscope according to the manufacturer's (Millipore) specifications. Phase contrast images showed that CRP-treated cells exhibited a dose-dependent increase in bone matrix deposition. Increased bone matrix deposition was also detectable by fluorescence microscopy. Non-amidated CRP had no effect on bone matrix formation.

The sequence specificity of the effect of CRP on bone matrix formation was evaluated using the scrambled peptide, {pGln}NFWQWWIQARKQ (SEQ ID NO:51), which was amidated at the C-terminus. hFOB cells were treated as described above with 18.4 µM of the scrambled peptide, and bone matrix formation was assayed with the Millipore Osteogenesis Quantitation kit as described above. The scrambled peptide did not induce bone matrix formation, indicating that CRP had a sequence-specific effect on bone matrix formation.

We also tested the effect of CRP on osteocalcin, a regulator of bone matrix production, in the hFOB cell line. The cells were treated with 4.6 or 13.8 µM CRP for 48 hours, then harvested and processed to obtain cellular protein extracts. Extracts were analyzed by SDS-PAGE and immunoblotted with a polyclonal anti-osteocalcin antibody. We found a dose-dependent increase in levels of osteocalcin in CRP-treated cells.

Example 5

Effect of CRP on Fracture Healing and the Formation of Bone Matrix

We simulated fractures (wounds) in confluent osteoblast cultures of hFOB cells by mechanically dissociating cells, and we then treated the wounded cultures with CRP. The cells were then treated with 50% DMSO or 13.8 µM CRP, each for 24 hours. The cells were then fixed with 70% ethanol, washed with PBS, and photographed using an Olympus-IMT microscope. As shown in FIG. 3, a line of disruption, lacking confluent cells, is apparent soon after the simulated wound. After 24 hours, the wound was still visible in control, DMSO-treated cells, but was not visible following CRP treatment.

In cell culture, we also studied the effect of amino acid substitutions in CRP on the formation of bone matrix. hFOB cells were treated with human CRP (KRQWAQFKIQWNQR; SEQ ID NO:42) and, separately, mouse CRP (KRQWTQFKIQWSQR; SEQ ID NO:43) before staining with Alizarin dye to identify the matrix that is formed. Fluorescent images were acquired using an Olympus-IMP microscope. As shown in FIG. 4, no calcium deposits were evident in an untreated culture, but treatment with both 12.5 µM hCRP and 12.5 µM mCRP produced calcium deposits.

Example 6

CRP Localization in Bone Fractures

Figure 5:
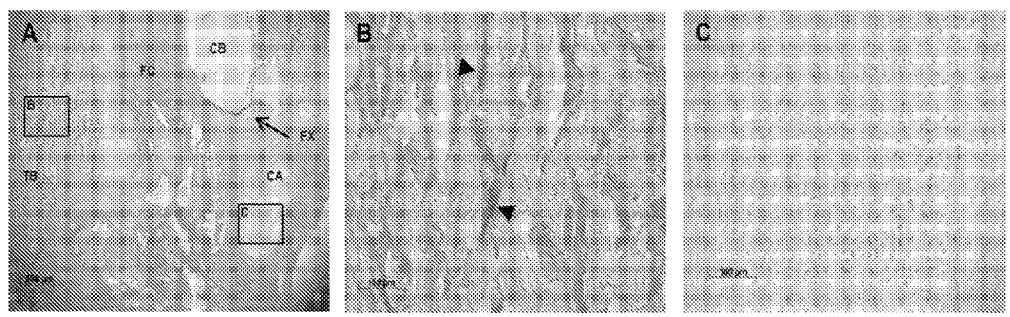
FIG. 5 is a panel of histomicrographs from a rat fracture callus stained with anti-CRP antibodies (DAB detection). The low magnification image (A) shows the fracture site (FX, arrow) with regions of trabecular bone (TB), cortical bone (CB), fibrocartilage (FC), and cartilage (CA). An image obtained at higher magnification (B) shows positive immunoreactivity in large lining cells (arrowheads). An image obtained at higher magnification of a region of cartilage (C) shows a lack of reactivity.

We probed sections from a post-fracture day 10 rat fracture callus with an anti-CRP antibody, followed by DAB for detection. As shown in FIG. 5, an image obtained at low magnification (left-hand panel; A) showed the fracture site (FX, arrow) with regions of trabecular bone (TB), cortical bone (CB), fibrocartilage (FC), and cartilage (CA). Diffuse staining was seen in regions of fibrocartilage and osteoid, with more punctate staining seen in regions of trabecular bone. A higher magnification image of the region of trabecular bone contained within the region boxed in the left-hand panel, is shown in the center panel (B), with arrows highlighting positive immunoreactivity in large lining cells. A higher magnification image of a region of cartilage boxed in the left-hand panel, is shown in the right-hand panel (C). No labeling was seen in this region of cartilage.

Example 7

Micro-CT Results of Femur in CRP-Treated Ovariectomized Rats

Figure 6:
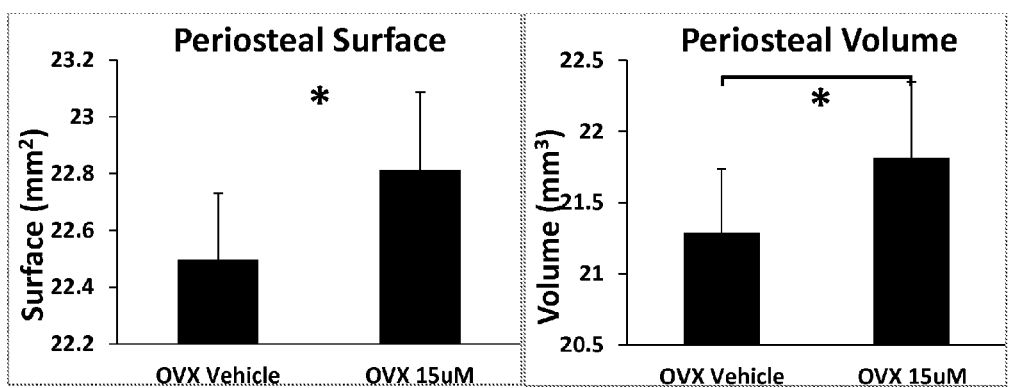
FIG. 6 is a pair of bar graphs illustrating data obtained from micro-computed tomography of cortical bone from the femoral midshafts of ovariectomized rats treated with either a vehicle-only control or rat CRP. The graphs plot the periosteal surface ($mm^2$) and periosteal volume ($mm^3$), which are both greater following CRP treatment.
Figure 7:
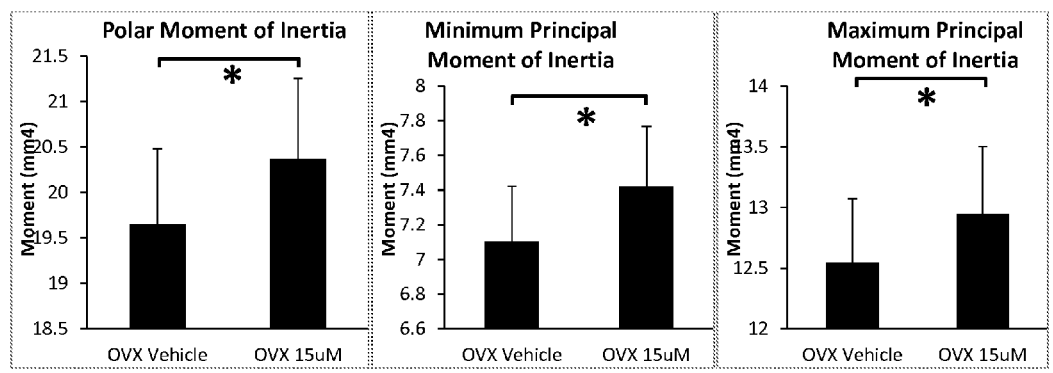
FIG. 7 is a panel of bar graphs illustrating data obtained from micro-computed tomography of cortical bone from the femoral midshafts of ovariectomized rats treated with either a vehicle-only control or rat CRP. The graphs plot the average polar moment of inertia, the maximum principal moment of inertia, and the minimum principal moment of inertia, all of which were significantly greater following CRP treatment.

We performed a micro-CT analysis of cortical bone from the femoral midshafts of ovariectomized (OVX) rats treated with 50% DMSO (OVX Vehicle) or 15 µM rat CRP (OVX 15 µM). Sprague Dawley rats (n=12/group) were ovariectomized at 6 months of age and allowed to lose bone for one month prior to treatment. They were then administered vehicle or 15 µM CRP (1 mL), via intraperitoneal injection, five times per week for five weeks. The animals were then sacrificed and their femora were harvested. The femora were scanned using microCT (Scanco uCT40) and 1.8 mm-long mid-diaphyseal regions of interest were analyzed. The results shown in FIG. 6 demonstrate that the average periosteal volume and periosteal surface were significantly greater in CRP-treated rats ($p<0.05$ using ANCOVA). Similarly, as shown in FIG. 7, the average polar moment of inertia, the maximum principal moment of inertia, and the minimum principal moment of inertia, were all significantly greater following CRP treatment ($p<0.05$ using ANCOVA).

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a patient who is at risk for, or who has been diagnosed as having, a compromised bone, the method comprising administering to the patient a therapeutically effective amount of a pharmaceutical composition comprising a substantially pure polypeptide comprising a fragment of a calcitonin receptor, wherein the polypeptide comprises an amino acid sequence conforming to:

```
                                          (SEQ ID NO:4);
Trp-Ala-Gln-Phe-Lys-Ile-Gln-Trp-Asn-Gln-Arg-Trp (SEQ ID NO:5);
Trp-Val-Gln-Phe-Lys-Ile-Gln-Trp-Asn-Gln-Arg-Trp (SEQ ID NO:6);
Trp-Thr-Gln-Phe-Lys-Ile-Gln-Trp-Ser-Gln-Arg-Trp
or
                                          (SEQ ID NO:7),
Trp-Ala-Gln-Phe-Lys-Ile-Gln-Trp-Ser-His-Arg-Trp
``` and wherein the polypeptide is 12-18 amino acids in length and is amidated at the C-terminus.

2. The method of claim 1, wherein the compromised bone comprises cancerous cells.

3. The method of claim 1, wherein the compromised bone is associated with a bone disorder.

4. The method of claim 3, wherein the bone disorder is osteoporosis, osteopenia, osteomalacia or rickets.

5. The method of claim 1, wherein the compromised bone is a fractured bone.

6. The method of claim 1, wherein the patient is a human patient.

7. The method of claim 6, wherein the human patient is more than about 50 years old.

8. The method of claim 1, wherein the polypeptide comprises Trp-Ala-Gln-Phe-Lys-Ile-Gln-Trp-Asn-Gln-Arg-Trp (SEQ ID NO:4).

9. The method of claim 1, wherein the polypeptide comprises Trp-Val-Gln-Phe-Lys-Ile-Gln-Trp-Asn-Gln-Arg-Trp (SEQ ID NO:5).

10. The method of claim 1, wherein the polypeptide comprises Trp-Thr-Gln-Phe-Lys-Ile-Gln-Trp-Ser-Gln-Arg-Trp (SEQ ID NO:6).

11. The method of claim 1, wherein the polypeptide comprises Trp-Ala-Gln-Phe-Lys-Ile-Gln-Trp-Ser-His-Arg-Trp (SEQ ID NO:7).

12. The method of claim 6, wherein the polypeptide further comprises, at the amino terminus of the polypeptide: a glutamate (Glu) residue; a pyroglutamate (pGlu) residue; or the amino acid sequence Lys-Arg-Gln.

13. The method of claim 1, wherein the polypeptide comprises an amino acid sequence conforming to:

```
                                          (SEQ ID NO:8);
Glu/pGlu-Trp-Ala-Gln-Phe-Lys-Ile-Gln-Trp-Asn-Gln-
Arg-Trp (SEQ ID NO:9);
Glu/pGlu-Trp-Val-Gln-Phe-Lys-Ile-Gln-Trp-Asn-Gln-
Arg-Trp (SEQ ID NO:10);
Glu/pGlu-Trp-Thr-Gln-Phe-Lys-Ile-Gln-Trp-Ser-Gln-
Arg-Trp
or
                                          (SEQ ID NO:11)
Glu/pGlu-Trp-Ala-Gln-Phe-Lys-Ile-Gln-Trp-Ser-His-
Arg-Trp.
```

14. The method of claim 1, wherein the polypeptide comprises an amino acid sequence conforming to:

Lys-Arg-Gln-Trp-Ala-Gln-Phe-Lys-Ile-Gln-Trp-Asn-Gln-Arg-Trp (SEQ ID NO:12);

Lys-Arg-Gln-Trp-Val-Gln-Phe-Lys-Ile-Gln-Trp-Asn-Gln-Arg-Trp (SEQ ID NO:13);

Lys-Arg-Gln-Trp-Thr-Gln-Phe-Lys-Ile-Gln-Trp-Ser-Gln-Arg-Trp (SEQ ID NO:14); or

Lys-Arg-Gln-Trp-Ala-Gln-Phe-Lys-Ile-Gln-Trp-Ser-His-Arg-Trp (SEQ ID NO:15).

15. The method of claim 1, wherein the polypeptide consists of an amino acid sequence conforming to:

```
                                          (SEQ ID NO: 4)
Trp-Ala-Gln-Phe-Lys-Ile-Gln-Trp-Asn-Gln-Arg-Trp;

(SEQ ID NO: 5)
Trp-Val-Gln-Phe-Lys-Ile-Gln-Trp-Asn-Gln-Arg-Trp;

(SEQ ID NO: 6)
Trp-Thr-Gln-Phe-Lys-Ile-Gln-Trp-Ser-Gln-Arg-Trp;

(SEQ ID NO: 7)
Trp-Ala-Gln-Phe-Lys-Ile-Gln-Trp-Ser-His-Arg-Trp;

(SEQ ID NO: 8)
Gln/pGln-Trp-Ala-Gln-Phe-Lys-Ile-Gln-Trp-Asn-Gln-Arg-Trp;

(SEQ ID NO: 9)
Gln/pGln-Trp-Val-Gln-Phe-Lys-Ile-Gln-Trp-Asn-Gln-Arg-Trp;

(SEQ ID NO: 10)
Gln/pGln-Trp-Thr-Gln-Phe-Lys-Ile-Gln-Trp-Ser-Gln-Arg-Trp;

(SEQ ID NO: 11)
Gln/pGln-Trp-Ala-Gln-Phe-Lys-Ile-Gln-Trp-Ser-His-Arg-Trp;

(SEQ ID NO: 12)
Lys-Arg-Gln/pGln-Trp-Ala-Gln-Phe-Lys-Ile-Gln-Trp-Asn-Gln-Arg-Trp;
```

-continued (SEQ ID NO: 13)
Lys-Arg-Gln/pGln-Trp-Val-Gln-Phe-Lys-Ile-Gln-Trp-Asn-Gln-Arg-Trp;

(SEQ ID NO: 14)
Lys-Arg-Gln/pGln-Trp-Thr-Gln-Phe-Lys-Ile-Gln-Trp-Ser-Gln-Arg-Trp;

(SEQ ID NO: 15)
Lys-Arg-Gln/pGln-Trp-Ala-Gln-Phe-Lys-Ile-Gln-Trp-Ser-His-Arg-Trp.

16. The method of claim 1, wherein the pharmaceutical composition is formulated for parenteral administration.

17. The method of claim 16, wherein the parenteral administration is intravenous administration.

* * * * *

SEQUENCE LISTING

<160> NUMBER OF SEQ ID NOS: 51

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala, Val, Thr or Asn
<220> FEATURE:
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (5)..(5)
<223> OTHER INFORMATION: Lys or Gln
<220> FEATURE:
<221> NAME/KEY: MOD_RES
<222> LOCATION: (6)..(6)
<223> OTHER INFORMATION: Ile or Ala
<220> FEATURE:
<221> NAME/KEY: MOD_RES
<222> LOCATION: (9)..(9)
<223> OTHER INFORMATION: Asn or Ser
<220> FEATURE:
<221> NAME/KEY: MOD_RES
<222> LOCATION: (10)..(10)
<223> OTHER INFORMATION: Gln or His

<400> SEQUENCE: 1

Trp Xaa Gln Xaa Xaa Xaa Gln Trp Xaa Xaa Arg Trp
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Val, Thr or Asn
<220> FEATURE:
<221> NAME/KEY: MOD_RES
<222> LOCATION: (7)..(7)
<223> OTHER INFORMATION: Phe or Tyr
<220> FEATURE:
<221> NAME/KEY: MOD_RES
<222> LOCATION: (8)..(8)
<223> OTHER INFORMATION: Lys or Gln
<220> FEATURE:
<221> NAME/KEY: MOD_RES
<222> LOCATION: (9)..(9)
<223> OTHER INFORMATION: Ile or Ala
<220> FEATURE:
<221> NAME/KEY: MOD_RES
<222> LOCATION: (12)..(12)
<223> OTHER INFORMATION: Asn or Ser
<220> FEATURE:
<221> NAME/KEY: MOD_RES
<222> LOCATION: (13)..(13)
<223> OTHER INFORMATION: Gln or His

<400> SEQUENCE: 2

Lys Arg Gln Trp Xaa Gln Xaa Xaa Xaa Gln Trp Xaa Xaa Arg Trp
1               5                   10                  15

```
<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala, Val, Thr or Asn
<220> FEATURE:
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (5)..(5)
<223> OTHER INFORMATION: Lys or Gln
<220> FEATURE:
<221> NAME/KEY: MOD_RES
<222> LOCATION: (6)..(6)
<223> OTHER INFORMATION: Ile or Ala
<220> FEATURE:
<221> NAME/KEY: MOD_RES
<222> LOCATION: (9)..(9)
<223> OTHER INFORMATION: Asn or Ser
<220> FEATURE:
<221> NAME/KEY: MOD_RES
<222> LOCATION: (10)..(10)
<223> OTHER INFORMATION: Gln or His

<400> SEQUENCE: 3

Trp Xaa Gln Xaa Xaa Xaa Gln Trp Xaa Xaa Arg Trp Gly Arg Arg
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ala Gln Phe Lys Ile Gln Trp Asn Gln Arg Trp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Val Gln Phe Lys Ile Gln Trp Asn Gln Arg Trp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Thr Gln Phe Lys Ile Gln Trp Ser Gln Arg Trp
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Ala Gln Phe Lys Ile Gln Trp Ser His Arg Trp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 8

Xaa Trp Ala Gln Phe Lys Ile Gln Trp Asn Gln Arg Trp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 9

Xaa Trp Val Gln Phe Lys Ile Gln Trp Asn Gln Arg Trp
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 10

Xaa Trp Thr Gln Phe Lys Ile Gln Trp Ser Gln Arg Trp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

<223> OTHER INFORMATION: Glu or pyroglutamate

<400> SEQUENCE: 11

Xaa Trp Ala Gln Phe Lys Ile Gln Trp Ser His Arg Trp
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Arg Gln Trp Ala Gln Phe Lys Ile Gln Trp Asn Gln Arg Trp
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Arg Gln Trp Val Gln Phe Lys Ile Gln Trp Asn Gln Arg Trp
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Arg Gln Trp Thr Gln Phe Lys Ile Gln Trp Ser Gln Arg Trp
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Arg Gln Trp Ala Gln Phe Lys Ile Gln Trp Ser His Arg Trp
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ala Gln Phe Lys Ile Gln Trp Asn Gln Arg Trp Gly Arg Arg
1               5                   10                  15

<210> SEQ ID NO 17

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Val Gln Phe Lys Ile Gln Trp Asn Gln Arg Trp Gly Arg Arg
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Thr Gln Phe Lys Ile Gln Trp Ser Gln Arg Trp Gly Arg Arg
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Ala Gln Phe Lys Ile Gln Trp Ser His Arg Trp Gly Arg Arg
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 20

Xaa Trp Ala Gln Phe Lys Ile Gln Trp Asn Gln Arg Trp Gly Arg Arg
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 21

Xaa Trp Val Gln Phe Lys Ile Gln Trp Asn Gln Arg Trp Gly Arg Arg
1               5                   10                  15

<210> SEQ ID NO 22
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 22

Xaa Trp Thr Gln Phe Lys Ile Gln Trp Ser Gln Arg Trp Gly Arg Arg
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 23

Xaa Trp Ala Gln Phe Lys Ile Gln Trp Ser His Arg Trp Gly Arg Arg
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Arg Gln Trp Ala Gln Phe Lys Ile Gln Trp Asn Gln Arg Trp Gly
1               5                   10                  15

Arg Arg

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Arg Gln Trp Val Gln Phe Lys Ile Gln Trp Asn Gln Arg Trp Gly
1               5                   10                  15

Arg Arg

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Arg Gln Trp Thr Gln Phe Lys Ile Gln Trp Ser Gln Arg Trp Gly
1               5                   10                  15
```

Arg Arg

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Arg Gln Trp Ala Gln Phe Lys Ile Gln Trp Ser His Arg Trp Gly
1               5                   10                  15

Arg Arg

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: May or may not be present
<220> FEATURE:
<221> NAME/KEY: MOD_RES
<222> LOCATION: (3)..(3)
<223> OTHER INFORMATION: Gln, pyroglutamate or absent
<220> FEATURE:
<221> NAME/KEY: MOD_RES
<222> LOCATION: (5)..(5)
<223> OTHER INFORMATION: Ala, Val, Thr or Asn
<220> FEATURE:
<221> NAME/KEY: MOD_RES
<222> LOCATION: (7)..(7)
<223> OTHER INFORMATION: Phe or Tyr
<220> FEATURE:
<221> NAME/KEY: MOD_RES
<222> LOCATION: (8)..(8)
<223> OTHER INFORMATION: Lys or Gln
<220> FEATURE:
<221> NAME/KEY: MOD_RES
<222> LOCATION: (9)..(9)
<223> OTHER INFORMATION: Ile or Ala
<220> FEATURE:
<221> NAME/KEY: MOD_RES
<222> LOCATION: (11)..(11)
<223> OTHER INFORMATION: May or may not be present
<220> FEATURE:
<221> NAME/KEY: MOD_RES
<222> LOCATION: (12)..(12)
<223> OTHER INFORMATION: Asn, Ser or absent
<220> FEATURE:
<221> NAME/KEY: MOD_RES
<222> LOCATION: (13)..(13)
<223> OTHER INFORMATION: Gln, His or absent
<220> FEATURE:
<221> NAME/KEY: MOD_RES
<222> LOCATION: (16)..(16)
<223> OTHER INFORMATION: May or may not be present
<220> FEATURE:
<221> NAME/KEY: MOD_RES
<222> LOCATION: (17)..(17)
<223> OTHER INFORMATION: May or may not be present
<220> FEATURE:
<221> NAME/KEY: MOD_RES
<222> LOCATION: (18)..(18)
<223> OTHER INFORMATION: May or may not be present
<220> FEATURE:

```
<221> NAME/KEY: MOD_RES
<222> LOCATION: (19)..(19)
<223> OTHER INFORMATION: May or may not be present

<400> SEQUENCE: 28

Lys Arg Xaa Trp Xaa Gln Xaa Xaa Xaa Gln Trp Xaa Xaa Arg Trp Ala
1               5                   10                  15

Gly Arg Arg

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Arg Gln Trp Asn Gln Tyr Gln Ala Gln Arg Trp Ala Gly Arg Arg
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 30

Xaa Trp Asn Gln Tyr Gln Ala Gln Arg Trp Ala
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Asn Gln Tyr Gln Ala Gln Arg Trp Ala
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Asn Gln Tyr Gln Ala Gln Arg Trp Ala Gly Arg Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Glu or pyroglutamate

<400> SEQUENCE: 33

Xaa Trp Asn Gln Tyr Gln Ala Gln Arg Trp Ala Gly Arg Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: May or may not be present
<220> FEATURE:
<221> NAME/KEY: MOD_RES
<222> LOCATION: (3)..(3)
<223> OTHER INFORMATION: Gln, pyroglutamate or absent
<220> FEATURE:
<221> NAME/KEY: MOD_RES
<222> LOCATION: (5)..(5)
<223> OTHER INFORMATION: Ala, Val, Thr or Asn
<220> FEATURE:
<221> NAME/KEY: MOD_RES
<222> LOCATION: (7)..(7)
<223> OTHER INFORMATION: Phe or Tyr
<220> FEATURE:
<221> NAME/KEY: MOD_RES
<222> LOCATION: (8)..(8)
<223> OTHER INFORMATION: Lys or Gln
<220> FEATURE:
<221> NAME/KEY: MOD_RES
<222> LOCATION: (9)..(9)
<223> OTHER INFORMATION: Ile or Ala
<220> FEATURE:
<221> NAME/KEY: MOD_RES
<222> LOCATION: (11)..(11)
<223> OTHER INFORMATION: May or may not be present
<220> FEATURE:
<221> NAME/KEY: MOD_RES
<222> LOCATION: (12)..(12)
<223> OTHER INFORMATION: Asn, Ser or absent
<220> FEATURE:
<221> NAME/KEY: MOD_RES
<222> LOCATION: (13)..(13)
<223> OTHER INFORMATION: Gln, His or absent

<400> SEQUENCE: 34

Lys Arg Xaa Trp Xaa Gln Xaa Xaa Xaa Gln Trp Xaa Xaa Arg
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Arg Gln Trp Ala Gln Phe Lys Ile Gln Trp Asn Gln Arg
1               5                   10
```

```
<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Gln Phe Asn Ala Trp Gln Trp Arg Ile Gln Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Gln Phe Gln Ile Arg Gln Ala Asn Lys Trp Trp
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asn Phe Trp Gln Trp Trp Ile Gln Ala Arg Lys Gln
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Asn Gln Tyr Gln Ala Gln Arg Trp
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or pyroglutamate

<400> SEQUENCE: 40

Xaa Trp Asn Gln Tyr Gln Ala Gln Arg Trp
1               5                   10

<210> SEQ ID NO 41
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 41

Lys Arg Gln Trp Asn Gln Tyr Gln Ala Gln Arg Trp
1               5                   10

<210> SEQ ID NO 42
<211> LENGTH: 14
<212> TYPE: PRT
<213> ORGANISM: Homo sapiens

<400> SEQUENCE: 42

Lys Arg Gln Trp Ala Gln Phe Lys Ile Gln Trp Asn Gln Arg
1               5                   10

<210> SEQ ID NO 43
<211> LENGTH: 14
<212> TYPE: PRT
<213> ORGANISM: Mus sp.

<400> SEQUENCE: 43

Lys Arg Gln Trp Thr Gln Phe Lys Ile Gln Trp Ser Gln Arg
1               5                   10

<210> SEQ ID NO 44
<211> LENGTH: 474
<212> TYPE: PRT
<213> ORGANISM: Homo sapiens

<400> SEQUENCE: 44

Met Arg Phe Thr Phe Thr Ser Arg Cys Leu Ala Leu Phe Leu Leu
1               5                   10                  15

Asn His Pro Thr Pro Ile Leu Pro Ala Phe Ser Asn Gln Thr Tyr Pro
                20                  25                  30

Thr Ile Glu Pro Lys Pro Phe Leu Tyr Val Val Gly Arg Lys Lys Met
            35                  40                  45

Met Asp Ala Gln Tyr Lys Cys Tyr Asp Arg Met Gln Gln Leu Pro Ala
        50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
    130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Arg Ser Leu
                165                 170                 175

Gly Cys Gln Arg Val Thr Leu His Lys Asn Met Phe Leu Thr Tyr Ile
            180                 185                 190

Leu Asn Ser Met Ile Ile Ile His Leu Val Glu Val Val Pro Asn
        195                 200                 205

Gly Glu Leu Val Arg Arg Asp Pro Val Ser Cys Lys Ile Leu His Phe
    210                 215                 220

-continued

```
Phe His Gln Tyr Met Met Ala Cys Asn Tyr Phe Trp Met Leu Cys Glu
225                 230                 235                 240

Gly Ile Tyr Leu His Thr Leu Ile Val Val Ala Val Phe Thr Glu Lys
            245                 250                 255

Gln Arg Leu Arg Trp Tyr Tyr Leu Leu Gly Trp Gly Phe Pro Leu Val
        260                 265                 270

Pro Thr Thr Ile His Ala Ile Thr Arg Ala Val Tyr Phe Asn Asp Asn
    275                 280                 285

Cys Trp Leu Ser Val Glu Thr His Leu Leu Tyr Ile Ile His Gly Pro
290                 295                 300

Val Met Ala Ala Leu Val Val Asn Phe Phe Leu Leu Asn Ile Val
305                 310                 315                 320

Arg Val Leu Val Thr Lys Met Arg Glu Thr His Glu Ala Glu Ser His
                325                 330                 335

Met Tyr Leu Lys Ala Val Lys Ala Thr Met Ile Leu Val Pro Leu Leu
            340                 345                 350

Gly Ile Gln Phe Val Val Phe Pro Trp Arg Pro Ser Asn Lys Met Leu
        355                 360                 365

Gly Lys Ile Tyr Asp Tyr Val Met His Ser Leu Ile His Phe Gln Gly
    370                 375                 380

Phe Phe Val Ala Thr Ile Tyr Cys Phe Cys Asn Asn Glu Val Gln Thr
385                 390                 395                 400

Thr Val Lys Arg Gln Trp Ala Gln Phe Lys Ile Gln Trp Asn Gln Arg
                405                 410                 415

Trp Gly Arg Arg Pro Ser Asn Arg Ser Ala Arg Ala Ala Ala Ala
            420                 425                 430

Ala Glu Ala Gly Asp Ile Pro Ile Tyr Ile Cys His Gln Glu Leu Arg
        435                 440                 445

Asn Glu Pro Ala Asn Asn Gln Gly Glu Glu Ser Ala Glu Ile Ile Pro
    450                 455                 460

Leu Asn Ile Ile Glu Gln Glu Ser Ser Ala
465                 470
```

<210> SEQ ID NO 45
<211> LENGTH: 18
<212> TYPE: PRT
<213> ORGANISM: Oryctolagus cuniculus

<400> SEQUENCE: 45

```
Lys Arg Gln Trp Val Gln Phe Lys Ile Gln Trp Asn Gln Arg Trp Gly
1               5                   10                  15

Arg Arg
```

<210> SEQ ID NO 46
<211> LENGTH: 18
<212> TYPE: PRT
<213> ORGANISM: Mus sp.

<400> SEQUENCE: 46

```
Lys Arg Gln Trp Thr Gln Phe Lys Ile Gln Trp Ser Gln Arg Trp Gly
1               5                   10                  15

Arg Arg
```

<210> SEQ ID NO 47
<211> LENGTH: 18
<212> TYPE: PRT

```
<213> ORGANISM: Rattus norvegicus

<400> SEQUENCE: 47

Lys Arg Gln Trp Ala Gln Phe Lys Ile Gln Trp Ser His Arg Trp Gly
1               5                   10                  15

Arg Arg

<210> SEQ ID NO 48
<211> LENGTH: 16
<212> TYPE: PRT
<213> ORGANISM: Sus scrofa

<400> SEQUENCE: 48

Lys Arg Gln Trp Asn Gln Tyr Gln Ala Gln Arg Trp Ala Gly Arg Arg
1               5                   10                  15

<210> SEQ ID NO 49
<211> LENGTH: 18
<212> TYPE: PRT
<213> ORGANISM: Homo sapiens

<400> SEQUENCE: 49

Lys Arg Gln Trp Ala Gln Phe Lys Ile Gln Trp Asn Gln Arg Trp Gly
1               5                   10                  15

Arg Arg

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Gln Arg Gln Lys Ile Trp Ala Phe Gln Asn Trp
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or absent

<400> SEQUENCE: 51

Xaa Asn Phe Trp Gln Trp Trp Ile Gln Ala Arg Lys Gln
1               5                   10
```